United States Patent [19]

Murakami et al.

[11] Patent Number: 4,552,760
[45] Date of Patent: Nov. 12, 1985

[54] METHOD FOR STABILIZING TISSUE PLASMINOGEN ACTIVATOR AND A STABLE AQUEOUS SOLUTION OR POWDER CONTAINING THE SAME

[75] Inventors: Akira Murakami, Tokyo; Hideo Yoshizaki, Saitama, both of Japan

[73] Assignees: Asahi Kasei Kogyo Kabushiki Kaisha; Kowa Co., Ltd., both of Japan

[21] Appl. No.: 603,063

[22] Filed: Apr. 23, 1984

[30] Foreign Application Priority Data

Apr. 21, 1983 [JP] Japan ................................. 58-69230

[51] Int. Cl.$^4$ ...................... C12N 9/50; A61K 31/715; A61K 35/12; A61K 35/48
[52] U.S. Cl. .................................. 424/94; 260/112 R; 260/117; 424/95; 424/105; 435/68; 435/188; 435/212; 435/215; 435/216; 435/219; 435/240
[58] Field of Search ................ 435/68, 215, 216, 212, 435/219, 188, 240; 424/94, 95, 105; 260/112 R, 117

[56] References Cited

U.S. PATENT DOCUMENTS

| | | | |
|---|---|---|---|
| 2,930,736 | 3/1960 | Sullivan et al. | 424/94 |
| 3,296,094 | 1/1967 | Cayle | 435/188 X |
| 3,322,632 | 5/1967 | Schwick et al. | 435/240 X |
| 3,998,947 | 12/1976 | D'Hinterland et al. | 424/105 |
| 4,083,961 | 4/1978 | D'Hinterland et al. | 424/105 |
| 4,151,161 | 4/1979 | Smith | 260/117 X |
| 4,245,051 | 1/1981 | Reich et al. | 435/212 |
| 4,264,493 | 4/1981 | Battista | 260/117 |
| 4,286,063 | 8/1981 | Suyama | 435/215 |
| 4,317,882 | 3/1982 | Horiguchi et al. | 435/212 |
| 4,495,285 | 1/1985 | Shimizu et al. | 435/215 |

FOREIGN PATENT DOCUMENTS

| | | | |
|---|---|---|---|
| 58-224687 | 12/1983 | Japan | 435/219 |
| 2119804 | 11/1983 | United Kingdom | 435/212 |

OTHER PUBLICATIONS

Biochimica et Biophysica Acta, 717 (1982), 327-336, Sueishi et al.

*Primary Examiner*—Howard E. Schain
*Attorney, Agent, or Firm*—Sughrue, Mion, Zinn, Macpeak, and Seas

[57] ABSTRACT

A method for stabilizing a tissue plasminogen activator which involves adding to an aqueous solution or powder containing a tissue plasminogen activator an effective amount of a purified gelatin is disclosed. A stable aqueous solution or powder which contains a tissue plasminogen activator and an effective amount of a purified gelatin is also disclosed. The method and composition eliminate the problem of adsorption of tissue plasminogen activator to various laboratory equipment, and also prevent the conversion of the single-chain tissue plasminogen activator into a double-chain tissue plasminogen activator.

20 Claims, 1 Drawing Figure

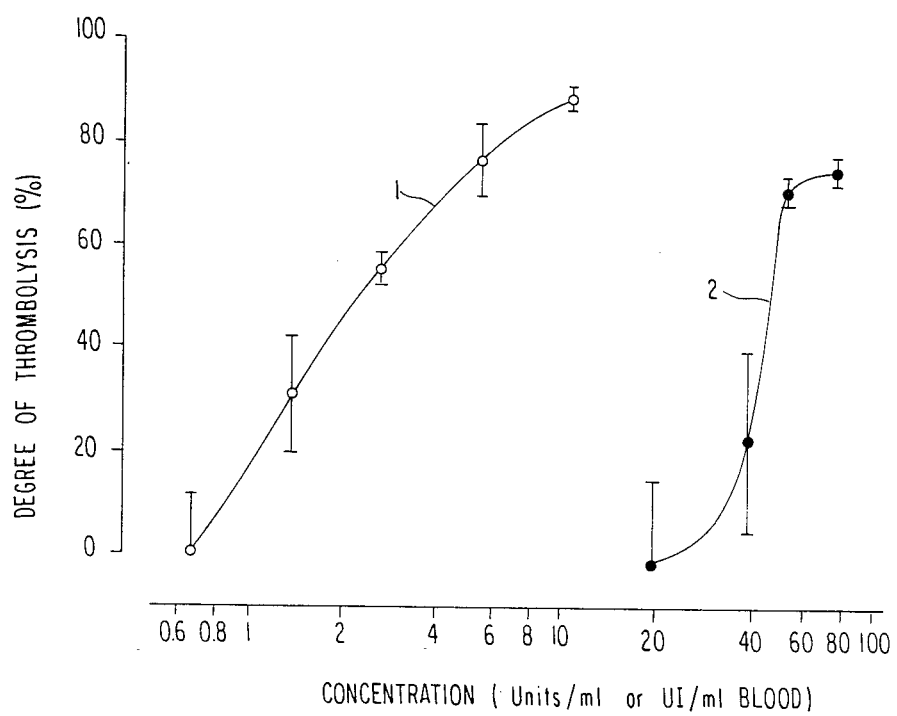

//  4,552,760

METHOD FOR STABILIZING TISSUE PLASMINOGEN ACTIVATOR AND A STABLE AQUEOUS SOLUTION OR POWDER CONTAINING THE SAME

FIELD OF THE INVENTION

This invention relates to a method for stabilizing a tissue plasminogen activator, and more particularly to a method for stabilizing a tissue plasminogen activator in which a purified gelatin is added to an aqueous solution or powder containing a tissue plasminogen activator. This invention also relates to a stable aqueous solution or powder which contains a tissue plasminogen activator and an effective amount of such a purified gelatin.

BACKGROUND OF THE INVENTION

In recent years various plastic materials have been used in the production of many medical appliances and analytical instruments.

At the same time, oligodynamic active substances such as proteins and glycoproteins isolated from animals and plants are under intensive studies for their application and development as drugs.

For stabilization or prevention of inactivation of these oligodynamic active substances, various stabilizers have heretofore been proposed. However, in administering the oligodynamic active substances, a problem arises in that there is a considerable difference between the activity as initially indicated and the practical effect obtained on administering the oligodynamic active substances in prescribed dosages.

This means, for example, that dosages to be administered to patients can not be precisely controlled and expensive drugs available only in small amounts are not used effectively.

As a result of extensive investigations to overcome the above-described problems, it has been found that the active substances are adsorbed onto the inner walls of, for example, test tubes, tubes, syringe cylinders, and bottles for nutrient fluids, which are made of glass or plastic materials such as polyethylene, polypropylene, and polystyrene, of medical appliances or analytical instruments, and that this adsorption is sometimes such that the percentage of the active substances being adsorbed reaches about 90%.

To prevent this adsorption phenomenon, silicone treatment has been applied or surface active agents have been used. These procedures, however, have disadvantages in that the effect is insufficient and their use as additives for drugs is not desirable.

At present, urokinase separated and purified from urine or cultured liquor of kidney cells and streptokinase collected from cultured liquor of Streptococci are plasminogen activators employed in practical use as thrombolytic agents.

However, since urokinase and streptokinase have poor affinity for fibrin, it is frequently necessary to administer urokinase and streptokinase in large amounts in order to obtain the required effect on treatment. When large doses are administered, side effects such as gastro-internal hemorrhage are manifested.

Further, plasmin formed in the circulating blood is likely to combine with a plasmin inhibitor in the blood, thereby losing activity rapidly. Therefore, in order to obtain the desired therapeutic effects, it is necessary for the enzymes to be administered in such large amounts as to result in the formation of plasmin in amounts exceeding that of the plasmin inhibitor contained in the blood. When, however, the plasmin is formed in such large amounts, the plasmin decomposes fibrinogen, causing side effects such as hemorrhage. On the other hand, those substances possessing high affinity for fibrin and capable of forming plasmin on the fibrin could decompose fibrin without being affected by the plasmin inhibitor contained in the circulating blood even when used in small amounts and would have only a reduced action to decompose fibrinogen present in the circulating blood.

Under such circumstances, a thrombolytic agent having high affinity for fibrin and high thrombolysing activity when administered in a small dose and having only a low level of side effects such as causing a gastro-internal hemorrhage has been eagerly sought.

As these plasminogen activators, tissue plasminogen activators (hereinafter referred to as "t-PA") present in tissues such as human or animal uterus, kidney, lung, small intestine, foreskin, and blood vesel walls, in culture liquors of normal cells originating from the foregoing tissues, or in culture liquors of tumor cells originating from the foregoing tissues or culture media of microorganisms or mammalian cells having t-PA-producing efficacy by genetic engineering have received increasing attention and are developed as thrombolytic agents. One of the present inventors has succeeded in obtaining t-PA from a tissue culture liquor of normal human tissue derived cells (European Patent Application (OPI) No. 0100982). Further, he has found that there are two types of t-PA: one having a single-chain structure and the other having a double-chain structure, and has reported that although there is almost no difference between the single-chain t-PA and the double-chain t-PA with respect to plasminogen activator (PA) activity and properties, the two forms of t-PA are different from each other in hydrolysis activity with the synthetic substrate t-butoxycarbonyl-phenylalanyl-serylaryginyl-methylcoumarine (Boc-Phe-Ser-Arg-MCA), and furthermore that the two forms of t-PA are different from each other in that upon reduction, the double-chain t-PA is decomposed, whereas the single-chain t-PA remains substantially undecomposed.

In addition, the present t-PA is more similar to t-PA found in the human body than those originating from animal tissues or tumor tissues and, therefore, is useful as a thrombolytic agent.

However, the present inventors' further investigations have revealed that with the present t-PA the same adsorption phenomenon to laboratory and medical equipment as described above occurs, thereby reducing the activity of the t-PA. It is therefore necessary to eliminate the problem of the adsorption phonomenon.

As a result of extensive investigations to discover a stabilizer which can be added to t-PA for use as a thrombolytic agent, it has been found that when purified gelatin is used, the adsorption can be prevented almost 100% and, furthermore, the active component adsorbed can be released and recovered. It has further been found, as a consequence of a study on the effect of the purified gelatin to prevent the adsorption of t-PA, that the purified gelatin acts to prevent the conversion of the single-chain t-PA into the double-chain t-PA.

SUMMARY OF THE INVENTION

Accordingly, one object of the present invention is to provide a method of stabilizing t-PA.

Another object of the present invention is to provide a stabilized composition containing t-PA.

These and other objects have been accomplished by providing a method for stabilizing t-PA which comprises adding an effective amount of a purified gelatin to an aqueous solution or powder containing t-PA.

The present invention also provides a stable aqueous solution or powder which contains a t-PA and an effective amount of a purified gelatin.

BRIEF DESCRIPTION OF THE DRAWING

FIGURE is a graph plotting the concentration against degree of thrombolysis for urokinase and t-PA, respectively.

DETAILED DESCRIPTION OF THE INVENTION

Purified gelatin is a product prepard from aqueous extract of raw collagen by heating. The raw collagen is obtained by acid or alkali treatment of the bone, skin, ligament or tendon of animals.

According to the present invention either a purified gelatin obtained by application of acid treatment or a purified gelatin obtained by application of alkali treatment can be used as the purified gelatin. The purified gelatin used in the present invention generally has an isoelectric point of from 4.5 to 9.0. Preferably an acid-treated gelatin having an isoelectric point of from 7.0 to 9.0 is used because the desired effect can be obtained by using lesser amounts of gelatin. Particularly preferred is a purified gelatin for injection as described in the Pharmacopoeia of Japan. The "purified" gelatin used herein means pharmaceutically acceptable gelatin. In general, the purified gelatin does not contain more than 20 ppm of heavy metals. Such purified gelatin is commercially available, such s "Difco gelatin" produced by Difco Co., "Merck gelatin" produced by Merck Co., "Haemaccel" produced by Hoechst A. G. and the like.

When the purified gelatin as used herein is administered to the human body, it is desirable to be of low molecular weight in order to avoid the problem of the purified gelatin being recognized as an antigen. The molecular weight is preferably between 3,000 and 50,000, and more preferably between 4,000 and 20,000.

The purified gelatin which is used as a stabilizer in the present invention has activity to prevent adsorption, activity to release t-PA adsorbed and, furthermore, activity to prevent conversion of the single-chain t-PA into the double-chain t-PA in t-PA consisting of the single-chain t-PA or composed of a mixture of the single-chain t-PA and double-chain t-PA.

The manner to add the purified gelatin is not critical. For example, the purified gelatin in a powdery form may be directly added to the t-PA solution. Alternatively, the powdery purified gelatin may be dissolved, in advance, in water or a suitable buffer, and then added to the t-PA solution. The powdery purified gelatin may also be mixed with the t-PA powder.

Addition of the purified gelatin may be effected at any time during the purification step or the step of manufacturing pharmaceutical preparations. It is preferred that the storage, purification and pharmaceutical preparations of the t-PA solution to which the purified gelatin is added be performed at a temperature of form 0° C. to 30° C., or more preferably from 0° C. to 10° C. When t-PA solution is stored in a frozen from, the temperature for storage is preferably maintained below 0° C., more preferably below −20° C.

By the addition of the purified gelatin, the t-PA activity of t-PA solution can be maintained during storage (regardless of whether it is in the form of solution or in a frozen form), the purification step or the step of manufacturing pharmaceutical preparations.

Further, the method for stabilizing t-PA according to the present invention is also applicable to lyophilization of t-PA. Illustratively stated, when t-PA solutions (especially, containing a highly purified t-PA) are subjected to lyophilization, the t-PA activity thereof generally markedly drops. However, t-PA solutions containing an effective amount of the purified gelatin can be lyophilized without losing the t-PA activity to give a t-PA powdery composition. The t-PA powdery composition may be dissolved to give a stable aqueous t-PA solution. Alternatively, the purified gelatin may be incorporated in the lyophilized t-PA preparations. When t-PA is stored in a powdedry form, it is preferred that the temperature for storage be maintained at 25° C. or below.

Although the amount of the purified gelatin to be added varies depending on the type of active component and the material of the vessel in which the final product is to be used, the amount of gelatin added is usually from 0.0001 to 0.10 g, preferably from 0.001 to 0.05 g, per mol of the aqueous solution having tissue plasminogen activator activity of 10 to 50,000 units/ml.

The t-PA as used herein can be obtained from tissues originating from humans or animals or tissue culture liquors derived from the foregoing tissues by application of techniques such as extraction and purification, examples of which are described below. Examples of the tissues and tissue culture cells include t-PA producing cells such as normal diploid cells originating from a human fetal kidney, a human fetal lung, a human fetal heart, a human fetal ureter, a human fetal skin, a human fetal foreskin and also from whole embryo; cells originating from a human placenta; normal diploid cells originating from a human kidney, a human intestine, a human lung, a human thyroid gland, a human heart, a human ureter and a human skin; human melanoma cells and tumor cells having similar properties; and cells originating from swine or bovine heart and swine or bovine uterus. Especially preferred are tissue culture liquors of normal diploid cells originating from a human fetal kidney, a human fetal lung and a human fetal foreskin.

A typical culture method is described below in the Reference Example.

As t-PA to be administered to the human body, those derived from human normal cells are preferred.

The t-PA which can be used in the present invention can be purified, for example, using fibrin Sepharose column chromatography utilizing a fibrin-bonded agarose, CM Sepharose column chromatography utilizing a carboxymethyl group-bonded agarose, ligand-exchange chromatography utilizing a zinc chelate agarose, lectin column chromatography utilizing a concanavalin A-bonded agarose, affinity chromatography using antibodies specific to the t-PA, and a gel filtration method utilizing crosslinked dextran particles.

A typical separation and purification method is described below.

To a tissue culture liquor of normal diploid cells originating from a human fetal kidney, lung, or foreskin, is added ammonium sulfate. The precipitate thus formed is dissolved in an acetate buffer, dialyzed against the same buffer, and adsorbed on a carboxymethyl cellulose column. Elution is then carried out by increasing the concentration of sodium chloride. The eluate is concentrated by ultrafiltration, dialyzed against a Tris-HCl acid buffer, and adsorbed on a lysine Sepharose column. Elution is then carried out by using ε-aminocapronic acid as an eluting solvent. The eluate thus obtained is again concentrated by ultrafiltration. The thus concentrated solution is gel-filtered by the use of Sephacryl S-200 Superfine (a trade name of Pharmacia Co.; a crosslinked product of N,N'-methylenebisacrylamide and allyldextran through covalent bonds), whereupon a plasminogen activator as used herein is obtained.

The thus-obtained t-PA is free from a variation in molecular weight since the polypeptide chain is bonded to the single chain through a disulfide linkage. However, t-PA is often obtained as a mixture containing the single-chain and double-chain forms, the double-chain form having been generated from the single-chain form by the action of proteinase during the process of purification. When conversion of the single-chain t-PA into the double-chain t-PA occurs, synthetic substrate decomposition activity such as the decomposition activity of Boc-Phe-Ser-Arg-MCA markedly increases. Since the double-chain t-PA is a product resulting from enzymatic decomposition of the naturally occurring single-chain t-PA, it is preferred to administer the natural-type single-chain t-PA, found in the living body, when using the t-PA as a thrombolyic agent in the human body. In order to obtain the single-chain t-PA, it is sufficient to include proteinase inhibitors such as aprotinine in the above-described purification step.

The titer measurement of the t-PA is carried out by the following procedures which were also used in the experiments described below.

Using an fibrin-added agar plate prepared by using 95% clotable fibrinogen (plasminogen content: about 50 casein units/g clotable protein) as a starting material, the measurement is carried out by a plate method employing urokinase as the standard. A solution of t-PA used in this invention is diluted with a 0.067M Tris-HCl buffer (pH 8.0) containing 1% gelatin, 0.1M sodium chloride and 0.1% sodium azide, and the concentration of the t-PA forming a lysing zone the same as that of 10 IU/ml of urokinase on the fibrin plate is designated as 10 units/ml.

The hydrolysis activity on a synthetic substrate of the t-PA is measured by the following procedures.

To 50 μl of either the t-PA used in this invention (100 units/ml) is added 0.1 mM of a synthetic substrate dissolved in 450 μl of a 0.05M Tris-HCl buffer (pH 8.0) containing 0.1M sodium chloride, and reaction is effected at 37° C. for 15 minutes. The reaction is terminated by adding 0.5 ml of 20% acetic acid, and then fluorometric measurement for formed aminomethylcoumarin is carried out at an excitation wavelength of 370 nm, a slit width of 5 nm, an emission wavelength of 460 nm and a slit width of 5 nm to determine the hydrolysis activity.

The thrombolytic activity of the t-PA was measured by the Chandler's loop method (Quart. J. Exp. Physiol., 46, 1 (1961)). The degree of thrombosis as compared with that of urokinase is shown in FIGURE. The blood used was human fresh blood, the thrombus forming time was 30 minutes, and the thrombolysis time was 4 hours. In FIGURE, curve 1 is for the t-PA and curve 2 is for urokinase.

As a result, it was confirmed that the thrombolytic activity of t-PA was 30 times as strong as that of urokinase. Therefore, the t-PA is extremely useful as a thrombolytic agent which provides a strong thrombolytic effect upon administration of a small dose.

The t-PA used in this invention is preferably administered intravenously, and the dose, although varying depending on the condition of the patient, may be in the range of 200–1,000,000 units per day. The method for intravenous administration is preferably by injection, or it may be administered by dissolving in a transfusion medium etc.

The t-PA can be formulated into e.g., an injectable preparation, for example, by mixing the t-PA with, other than the purified gelatin, a conventional excipient for injection, a buffer (e.g., phosphate, sodium chloride, etc.), an isotonic agent, a filler (e.g., mannitol, dextran, cyclodextrin, etc.), a stabilizer (e.g., albumin, sulfites, etc.) or the like, dissolving the mixture in distilled water for injection, and freeze-drying and/or vacuum-drying the solution to obtain a drug composition which is filled in a vial for injection.

Other application of the t-PA, in addition to medical use as a thrombolytic agent, are for preventing the formation of a thrombus by, for example, combining it with materials such as artificial blood vessels, artificial organs etc., or as a diagnostic agent for thrombosis etc.

The present invention will be explained in more detail below by reference to the following non-limiting examples.

REFERENCE EXAMPLE

Human embryonic lung cells were seeded in a 500-ml spinner flask at a density of 105 cells/ml together with Cytodex I (dextran bead carrier for cell culture, registered trademark by Pharmacia Co.) at a concentration of 2.5 mg/ml, and a suspension was cultured by using 300 ml of MEM Medium containing 10% fetal calf serum as a growth medium at 37° C. in air containing 5% carbon dioxide, while stirring at a rotation of 60 rpm. After sufficient proliferation of the cells ($1.0 \times 10^6$ cells/ml) by their cultivation for 8 days, the bead carrier to which the cells had been adhereed was washed with physiological saline, and the medium was replaced by 300 ml of serum-free Medium 199 containing 0.5% lacto-albumin hydrolysate and cultivation was continued for 25 days with stirring at a rotation of 60 rpm. The medium was replaced on every fifth day. The cultured liquor containing the t-PA used in this invention was then recovered.

One liter of a human embryonic lung tissue cultured liquor thus obtained was passed through an anti-urokinase Ig-G Sepharose column, and then adsorbed onto a fibrin Sepharose column ($1.5 \times 10$ cm). After washing sufficiently with a 0.5M sodium chloride solution containing 0.1% Tween 80, a 0.5M arginine solution containing 0.1% Tween 80 was used to elute and collect 50 ml of a fraction containing the t-PA. The activity of this solution was 62 units/ml and the specific activity was 950 units/A280. This solution was dialyzed against physiological saline containing 0.1% Tween 80, then adsorbed onto a cancanavalin A Sepharose column ($1 \times 20$ cm), and washed with a 0.01M phosphate buffer (pH 7.0) containing 1M sodium chloride and 0.1% Tween 80, followed by eluting the t-PA according to a linearly gradient elution method using the above buffer at an initial stage while continuously changing the composition of buffer to a 0.01M phosphate buffer (pH 7.0) containing 0.4M methylmannoside, 2M ammonium thiocyanate and 0.1% Tween 80. The obtained solution was 25 ml in liquid volume, and the activity was 98 units/ml and its specific activity was 5500 units/A280. After dialysis, the dialysate was concentrated by ultrafiltration and gel filtered by Sephadex G-150 to recover a 15 ml fraction containing activity. The activity was 135 units/ml and the specific activity was 12500 units-/A280.

EXAMPLE 1

Stabilization Effect for Test Tubes of Polyethylene (Adsorption-Preventing Effect)

To 180 μl of a physiological saline solution containing a stabilizer as described in Table 1 was added 20 μl of a physiological saline solution containing a given drug, and the resulting mixture was allowed to stand at 25° C. for 3 hours. Then the activity of the drug in the solution was measured to determine the residual activity rate.

As the drug, t-PA solution obtained in the Reference Example which had been adjusted to a concentration of 40 units/ml was used.

The results are shown in Table 1. In Run No. 1, no stabilizer was added (control) and in Run No. 2, a surface active agent (Tween 80) was used (comparative example).

The residual activity rate was calculated by the following equation:

$$\text{Residual Activity Rate (\%)} = \frac{\text{Residual Activity}}{\text{Initial Activity}} \times 100$$

TABLE 1

| Run No. | Stabilizer Type | Amount (%) | Residual Activity Rate (%) |
|---|---|---|---|
| 1 (control) | — | — | 11 |
| 2 (comparative example | Tween 80 | 0.05 | 99 |
| 3 | Purified gelatin (1)* | 0.1 | 55 |
| | | 0.3 | 67 |
| | | 1.0 | 100 |
| 4 | Purified gelatin (2)* | 0.1 | 29 |
| | | 0.3 | 34 |
| | | 1.0 | 41 |

*(1) Acid-treated; Isoelectric point : 7.0–9.0; molecular weight: 7,000 ± 2,000
*(2) Alkali-treated; Isoelectric point : 4.5–5.0; molecular weight: 7,000 ± 2000

EXAMPLE 2

Stabilization Effect for Silicone-Treated Glass (Adsorption-Preventing Effect)

In the same manner as in Example 1, the residual activity rate was measured for glass test tubes treated with silicone. The results are shown in Table 2 below.

TABLE 2

| Run No. | Stabilizer Type | Amount (%) | Residual Activity Rate (%) |
|---|---|---|---|
| 1 (control) | No addition | — | 59 |
| 2 (comparative example) | Tween 80 | 0.05 | 122 |
| 3 | Purified gelatin (1)* | 0.01 | 44 |
| | | 0.1 | 92 |
| | | 1.0 | 108 |
| 4 | Purified gelatin (2)* | 0.01 | 62 |
| | | 0.1 | 79 |
| | | 1.0 | 95 |

*Same as in Example 1

EXAMPLE 3

Effect of Release and Recovery from Test Tube of Polyethylene (1) In the same manner as in Example 1, a physiological saline solution with or without the stabilizer of the present invention was incubated at 25° C. for 3 hours with agitation and then measured for the activity of the drug in the solution to determine the residual activity rate. (2) After 3 hour incubation, the solution was discarded, and 200 μl of a physiological saline solution containing the stabilizer of the present invention was then placed in the test tube as an eluting solution. The solution was incubated at 25° C. for 1 hour with agitation. Then the activity of the drug in the solution was measured to determine the activity recovery rate.

The results are shown in Table 3.

TABLE 3

| Run No. | Stabilizer (Amount) | Residual Activity Rate (%) | Eluting Solution | Activity Recovery Rate (%) | Total Activity (%) |
|---|---|---|---|---|---|
| 1 | No addition | 60 | No addition | 0 | 60 |
| | | | Purified gelatin (1)* (1%) | 40 | 100 |
| 2 | No addition | 53 | No addition | 0 | 53 |
| | | | Tween 80 (0.05%) | 44 | 97 |
| 3 | Tween 80 (0.05%) | 120 | Tween 80 (0.05%) | 5 | 125 |
| 4 | Purified gelatin (1)* (1%) | 101 | Purified gelatin (1)* (1%) | 5 | 106 |

*Same as in Example 1

EXAMPLE 4

Effect in Preventing Conversion of Single-Chain t-PA into Double-Chain t-PA (1) Effectiveness of various types of gelatin To an aqueous solution containing 0.15M sodium chloride and 0.02% Tween 80 was added the single-chain t-PA at a concentration of 100 units/ml. Various types of gelatin as shown in Table 4 were each added to the solution as a stabilizer. Each solution was incubated at 37° C. for the predetermined periods, 0 day, 2 days and 5 days, and then measured for PA activity by the fibrin plate method to determine the residual activity rate and the hydrolysis activity for a synthetic substrate, Boc-Phe-Ser-Arg-MCA.

The results are shown in Table 4.

TABLE 4

| Run No. | Stabilizer Type[4] | Amount (%) | Residual Activity Rate (%) 2 days | Residual Activity Rate (%) 5 days | Hydroylsis Activity (%)[3] 0 days | Hydroylsis Activity (%)[3] 2 days | Hydroylsis Activity (%)[3] 5 days |
|---|---|---|---|---|---|---|---|
| 1 | Purified gelatin (1) | 1 | 97.4 | 95.5 | 49 | 55 | 53 |
| 2 | Purified gelatin (1) | 5 | 100.7 | 93.2 | 51 | 56 | 51 |
| 3 | Purified | 1 | 99.7 | 99.0 | 51 | 64 | 80 |

TABLE 4-continued

| Run No. | Stabilizer Type[4] | Amount (%) | Residual Activity Rate (%) 2 days | 5 days | Hydroylsis Activity (%)[3] 0 days | 2 days | 5 days |
|---|---|---|---|---|---|---|---|
| | gelatin (2) | | | | | | |
| 4 | Difco gelatin | 1 | 97.7 | 96.2 | 49 | 65 | 80 |
| 5 | Merck gelatin | 1 | 97.2 | 94.1 | 51 | 60 | 66 |
| 6 | Haemaccel | 1 | 103.5 | 97.1 | 47 | 55 | 76 |
| 7 | No addition[5] | | | | | | |
| *** | | | | | | | |
| | Single-chain t-PA | | 95.2 | 92.7 | 54 | 118 | 139 |
| | Double-chain t-PA | | 98.2 | 95.8 | 140 | 139 | 137 |

[3]Calculated with 1 μM AMC as 100%
[4](1), (2): Same as in Example 1
Difco gelatin: produced by Difco Co.
Merck gelatin: produced by Merck Co.
Haemaccel: produced by Hoechst A.G.
[5]Containing 1% albumin.

It is seen from the results that albumin which is well known as a stabilizer for an injectionable preparation cannot effectively prevent the convention of the single-chain t-PA into the double-chain t-PA and albumin has poor stabilizing effect for the single-chain t-PA.

(2) Dependency on Amount

To a solution as prepared in the same manner as in (1) above was added 0.1% or 1% of a stabilizer, and the resulting solution was stored at 4° C. for the predetermined periods, 0 day, 10 days, and 20 days, and then measured for the PA activity and the hydrolysis activity to a synthetic substrate.

The results are shown in Table 5 below.

TABLE 5

| Run No. | Stabilizer Type | Amount (%) | Residual Activity Rate (%) 10 days | 20 days | Hydrolysis Activity (%) 0 day | 10 days | 20 days |
|---|---|---|---|---|---|---|---|
| 1 (control) | No addition | — | 90.2 | 82.0 | 40 | 40 | 58 |
| 2 | Purified gelatin (1)* | 1 | 102.4 | 100.4 | 36 | 39 | 37 |
| 3 | Purified gelatin (1)* | 0.1 | 98.8 | 98.1 | 39 | 46 | 52 |

*Same as in Example 1

A sample of the present invention was reduced with 2% mercaptoethanol and then was subjected to electrophoresis using SDS polyacrylamide to determine the molecular weight fractions. This analysis showed that the reduced sample was substantially the same as that prior to the reduction treatment.

On the other hand, in the case of other stabilizers not falling within the scope of the present invention, upon application of the reduction treatment, the samples were decomposed into three spots. This confirmed that conversion was into the double-chain t-PA when the stabilizers of the present invention were not used.

PREPARATION EXAMPLE

| Tissue plaminogen activator | 24,000 units/ml |
|---|---|
| Purified gelatin | 20 mg |
| Minnitol | 100 mg |
| Sodium chloride | 7.8 mg |
| Sodium phosphate | 15.4 mg |

The above ingredients were dissolved in 2 ml of distilled water for injection, placed in a sterile vial, and then were subjected to the following treatments to prepare a vial for injection.

Preliminary freezing at −30° to −40° C. for 2 hours,
Primary drying at −30° to +20° C. in a vacuum of 0.05 to 0.1 Torr for 35 hours, and
Secondary drying at 30° C. in a vacuum of 0.01 to 0.05 Torr for 5 hours.

While the invention has been described in detail and with reference to specific embodiments thereof, it will be apparent to one skilled in the art that various changes and modifications can be made therein without departing from the spirit and scope thereof.

What is claimed is:

1. A method for stabilizing a tissue plasminogen activator which comprises adding to an aqueous solution or powder containing a tissue plasminogen activator an effective amount of a purified gelatin having an isoelectric point of 7.0 to 9.0.

2. A method of claim 1, wherein the purified gelatin has a weight average molecular weight of 3,000 to 50,000.

3. A method of claim 2, wherein the purified gelatin has a weight average molecular weight of 4,000 to 20,000.

4. A method of claim 1, wherein the purified gelatin is added in an amount of 0.0001 to 0.10 g per ml of the aqueous solution having a tissue plasminogen activator activity of 10 to 50,000 units/ml.

5. A method of claim 2, wherein the purified gelatin is added in an amount of 0.0001 to 0.10 g per ml of the aqueous solution having a tissue plasminogen activator activity of 10 to 50,000 units/ml.

6. A method of claim 3, wherein the purified gelatin is added in an amount of 0.0001 to 0.10 g per ml of the aqueous solution having a tissue plasminogen activator activity of 10 to 50,000 units/ml.

7. A method of claim 1, which further comprises subjecting to lyophilization the resulting aqueous solution having said stabilizing agent added thereto.

8. A method of claim 2, which further comprises subjecting to lyophilization the resulting aqueous solution having said stabilizing agent added thereto.

9. A method of claim 3, which further comprises subjecting to lyophilization the resulting aqueous solution having said stabilizing agent added thereto.

10. A method of claim 4, which further comprises subjecting to lyophilization the resulting aqueous solution having said stabilizing agent added thereto.

11. A method of claim 5, which further comprises subjecting to lyophilization the resulting aqueous solution having said stabilizing agent added thereto.

12. A method of claim 6, which further comprises subjecting to lyophilization the resulting aqueous solution having said stabilizing agent added thereto.

13. A stable aqueous solution or powder which contains a tissue plasminogen activator and an effective amount of a purified gelatin having an isoelectric point of 7.0 to 9.0.

14. A stable aqueous solution or powder of claim 13, wherein the purified gelatin has a weight average molecular weight of 3,000 to 50,000.

15. A stable aqueous solution or powder of claim 14, wherein the purified gelatin has a weight average molecular weight of 4,000 to 20,000.

16. A stable aqueous solution or powder of claim 13, wherein the purified gelatin is added in an amount of 0.0001 to 0.10 g per ml of the aqueous solution having a tissue plasminogen activator activity of 10 to 50,000 units/ml.

17. A stable aqueous solution or powder of claim 15, wherein the purified gelatin is added in an amount of 0.0001 to 0.10 g per ml of the aqueous solution having a tissue plasminogen activator activity of 10 to 50,000 units/ml.

18. A stable aqueous solution or powder or claim 17, wherein the purified gelatin is added in an amount of 0.0001 to 0.10 g per ml of the aqueous solution having a tissue plasminogen activator of 10 to 50,000 units/ml.

19. A method of claim 1 wherein the tissue plasminogen activator has been obtained from human tissue.

20. A stable aqueous solution or powder of claim 13 wherein the tissue plasminogen activator has been obtained from human tissue.

* * * * *